United States Patent [19]

Rice

[11] Patent Number: 5,304,201
[45] Date of Patent: Apr. 19, 1994

[54] RADIAL ARM QUICK ADJUSTING ARTERY CLAMP

[75] Inventor: Delbert L. Rice, Vancouver, Wash.

[73] Assignee: Rice Mold Design Service, Inc., Vancouver, Wash.

[21] Appl. No.: 944,183

[22] Filed: Sep. 11, 1992

[51] Int. Cl.⁵ ............................................. A61B 17/00
[52] U.S. Cl. ................................. 606/201; 606/151
[58] Field of Search ................ 269/62, 63; 606/151, 606/201, 204, 204.15

[56] References Cited

U.S. PATENT DOCUMENTS

| | | | |
|---|---|---|---|
| 2,331,831 | 10/1943 | Gordon | 269/63 |
| 4,233,980 | 11/1980 | McRae et al. | 606/201 |
| 4,572,182 | 2/1986 | Royse | 606/201 |
| 4,832,692 | 5/1989 | Box et al. | 604/211 |
| 5,133,734 | 7/1992 | Lee | 606/201 |
| 5,137,514 | 8/1992 | Ryan | 604/99 |
| 5,197,972 | 3/1993 | Hakki | 606/201 |

OTHER PUBLICATIONS

PCT WO 92/08411, Semler et al, 29 May 92.

*Primary Examiner*—C. Fred Rosenbaum
*Assistant Examiner*—N. Kent Gring
*Attorney, Agent, or Firm*—Robert L. Harrington

[57] ABSTRACT

A adjustable clamping device for applying pressure to a puncture site of an artery. The clamping device has a radial arm movably supported on a column which extends from a base. A carrier movably mounted on the end of the arm supports a pressure pad. The radial arm extends in a parallel attitude over the base and may be adjusted vertically upwardly and downwardly in reference to the base and may also be pivoted in reference to the column. Lateral movement of the arm facilitates positioning the pressure pad over the puncture site. A releasable feed mechanism on the arm controls movement of the carrier and thus the pressure pad. With the feed mechanism engaged, rotation of the carrier provides a controlled feeding of the carrier relative to the arm. With the feed mechanism disengaged, the carrier may be rapidly advanced or retracted. Independent locking mechanisms are provided for clamping of the lateral movement of the arm separate from the vertical and pivotal movements.

7 Claims, 4 Drawing Sheets

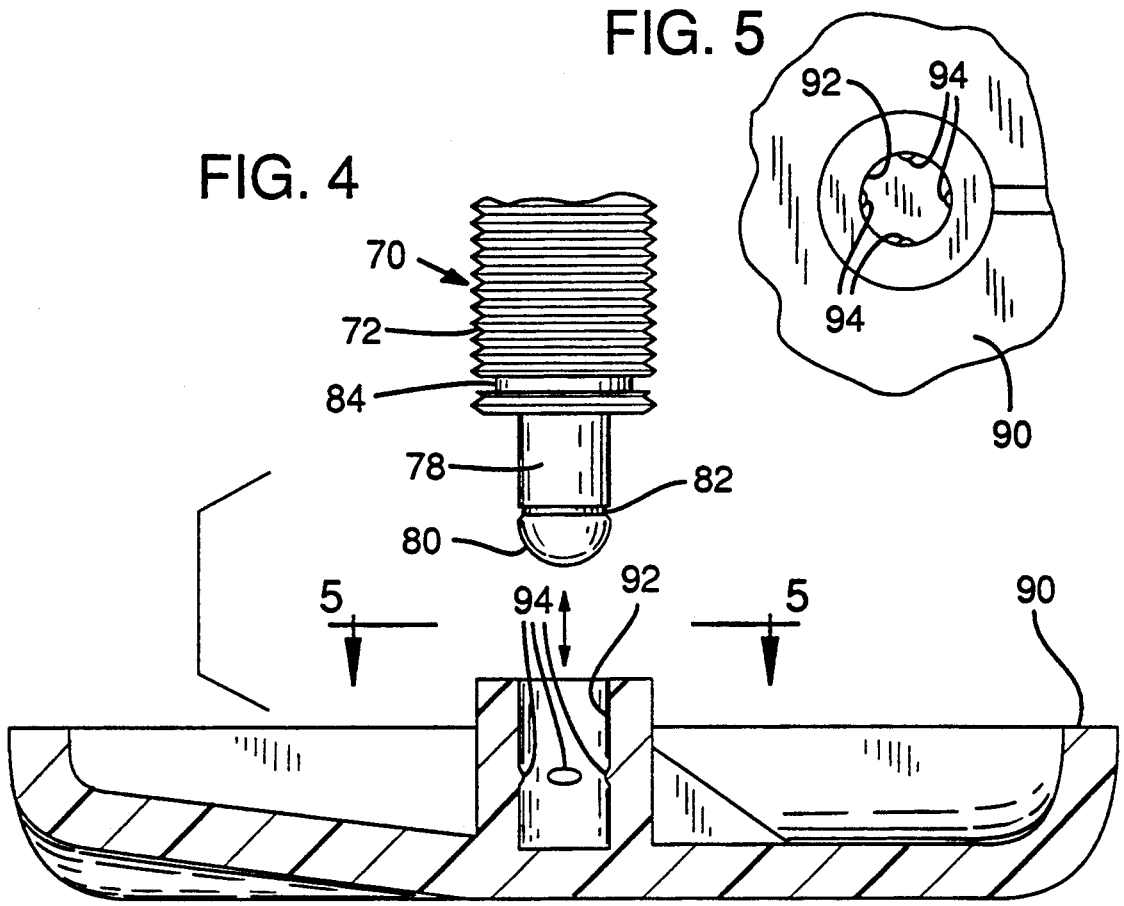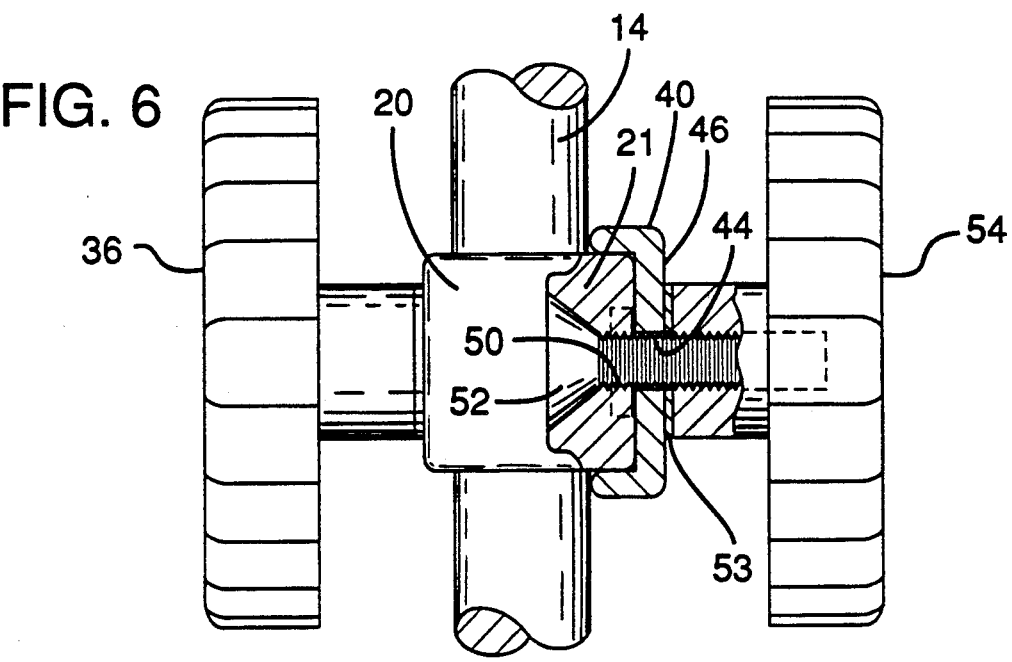

RADIAL ARM QUICK ADJUSTING ARTERY CLAMP

BACKGROUND INFORMATION

1. Field of the Invention

This invention relates to apparatus for applying pressure to a puncture site of an artery to arrest blood flow from the puncture upon removal of an instrument from the artery and particularly to a quick adjusting clamping mechanism for rapidly and finely controlling the pressure applied to a puncture site of an artery.

2. Background Information

It is well known in medical practice to penetrate an artery, such as a femoral artery, of a human by various instruments to extract a blood sample, inject fluids, insert instruments for diagnostic purposes and other procedures. The penetration of the artery produces an opening or wound and upon removal of the penetrating instrument bleeding occurs. It is necessary to apply pressure to the area of penetration particularly the puncture site to insure coagulation of the blood.

One of the methods employed is applying pressure to the area by an attendant's hand or fingers. This has been found to be less than satisfactory since it generally requires applying pressure for a number of minutes and the attendant is unable to perform other duties relating to the care of the patient. Further it is often difficult for the attendant to apply consistent pressure throughout the time period required.

To free the attendant for other duties and to provide a more consistent controlled clamping, mechanical clamping devices have been utilized to apply pressure to the puncture site to control bleeding. The clamping devices have a configured pad that is forcibly applied to the area of the puncture site to provide the necessary pressure to control the bleeding from the puncture.

One of the problems with the clamping device is the time required to place, position and adjust the clamp. The clamp must be positioned so that the pressure pad is strategically placed in reference to the puncture site so that the pressure pad may be forcibly placed against the puncture site at the desired time. A typical clamp has a base which is slid under the thigh of the patient to maintain the clamp in position. A vertical support member extends from the base and a lateral arm is movably mounted on the support with the arm extending over the base. The arm will thus be extended over the thigh when the clamp is positioned relative to the patient. A pressure pad is mounted on the end of the extended arm and extends downward in relation to the arm. The arm is pivoted and adjusted vertically on the vertical support and the arm is adjusted laterally relative to the vertical support to position the pressure pad over the puncture site. The arm is preferably positioned at a distance above the thigh so as not to hinder access to the puncture site, either visually or for instrument manipulation. The pressure pad is mounted on an adjusting screw so that the pad may be adjusted relative to the arm and thus may be advanced or retracted relative to the puncture site when the clamp is in position. The fine adjustment afforded by the adjusting screw provides control over the pressure applied to the puncture site by the pressure pad. Adjustment to either advance or retract the pressure pad any distance is, however, slow and time consuming. In many situations the adjusting screw must be rotated through a great number of revolutions to just advance the pressure pad so that it will contact the puncture site. Similarly, the adjusting screw must be rotated many revolutions to retract the pad away from the puncture site.

BRIEF SUMMARY OF THE INVENTION

The present invention is an artery clamp for applying a controlled pressure to a puncture site of an artery, such as a femoral artery in the thigh area of a human. The artery clamp of the present invention is of the type that has an arm extending over and movably mounted to a base. A carrier for holding a pressure pad is movably mounted to the arm. The pressure pad mounted on the carrier is utilized to apply pressure to an area of the puncture site. The clamp is positioned adjacent the patient with the base of the unit fitting under the thigh portion. The arm is extended over the top of the thigh with the pressure pad positioned above the puncture site. The clamp of the present invention includes features that facilitate rapid positioning adjustment and finely controlling the pressure applied to the puncture site by the pressure pad.

In a preferred embodiment the clamp of the present invention includes a novel feed mechanism on the arm that is releasably engageable with a carrier that supports a pressure pad. As previously mentioned, the clamp is usually placed adjacent the patient with the base of the clamp fitting under the thigh and the arm extending over the thigh area. The arm is adjusted to place the pressure pad over the puncture site of the artery. To facilitate rapid positioning of the pressure pad toward, that is to advance the pad to the area of the puncture site, the feed mechanism is arranged to be yieldably dis-engaged from the carrier. The feed mechanism is arranged so that forced urging of the carrier to advance will yieldably release the feed mechanism from the carrier permitting the carrier to be rapidly advanced (moved) and thus the pressure pad mounted on the carrier may be rapidly moved toward and into contact with the area of the puncture site. The feed mechanism may also be released from the carrier by moving the feed mechanism out of engagement with the carrier. With the feed mechanism moved out of engagement with the carrier, the carrier may be rapidly advanced or retracted as desired. The feed mechanism engaged with the carrier provides fine adjustment of the carrier movement to either advance or retract the carrier to accurately control the pressure applied to the puncture site by the pressure pad.

Refer now to the drawings and the detailed description for a complete understanding of the invention.

BRIEF DESCRIPTION OF THE DRAWINGS

FIG. 2A is a partial sectional view showing the carrier and quick release mechanism in the disengaged position;

FIG. 4 is a view of a pressure pad and the end of the carrier of the artery clamp;

FIG. 5 is a view of the pressure pad as viewed on view lines 5—5 of FIG. 4; and, FIG. 6 is a view as viewed on view lines 6—6 of FIG. 3 showing the mounting of the arm on the carriage.

DESCRIPTION OF THE PREFERRED EMBODIMENT

Figure 1:
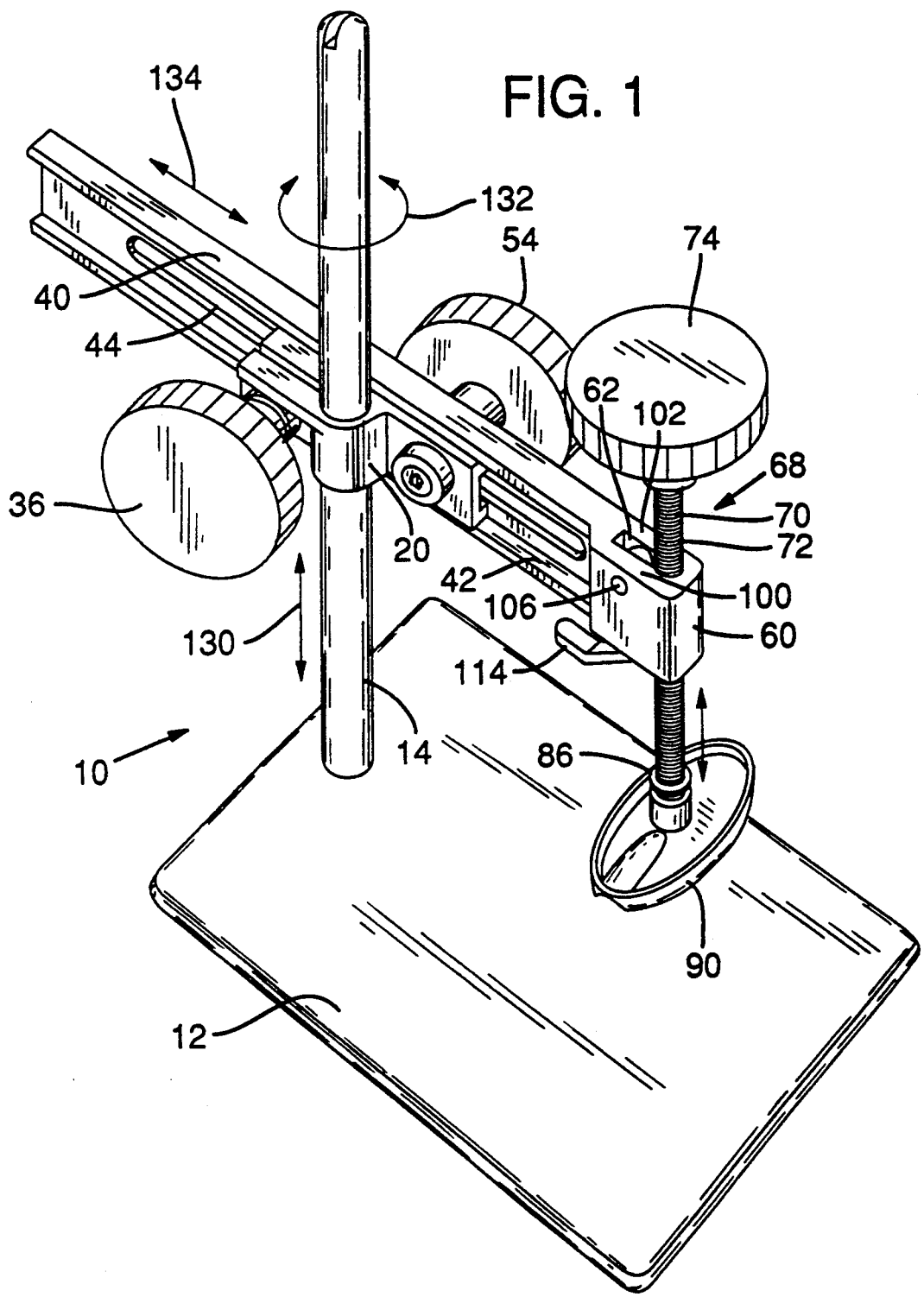
FIG. 1 is a perspective view of an adjustable radial arm artery clamp of the present invention.

Refer now to FIG. 1 of the drawings which illustrates a radial arm quick adjusting artery clamp 10 of the present invention. The clamp 10 is utilized in applying pressure to a puncture site of an artery. An artery is often penetrated in various medical and surgical procedures to facilitate insertion of a catheter for example. Upon removal of the catheter, or preferably coincident with the removal, pressure is applied to the puncture site to control bleeding and to allow coagulation of the blood to seal the puncture site. The clamp 10 is particularly suited to clamping a puncture site of a femoral artery. The ease of adjustment, the independent locking of the vertical and lateral movements and the quick release mechanism providing rapid advancement and retraction of the pressure pad in addition to the fine adjusting mechanism controlling the pressure applied by the pressure pad are some of the novel and useful features of the present invention.

Figure 2:
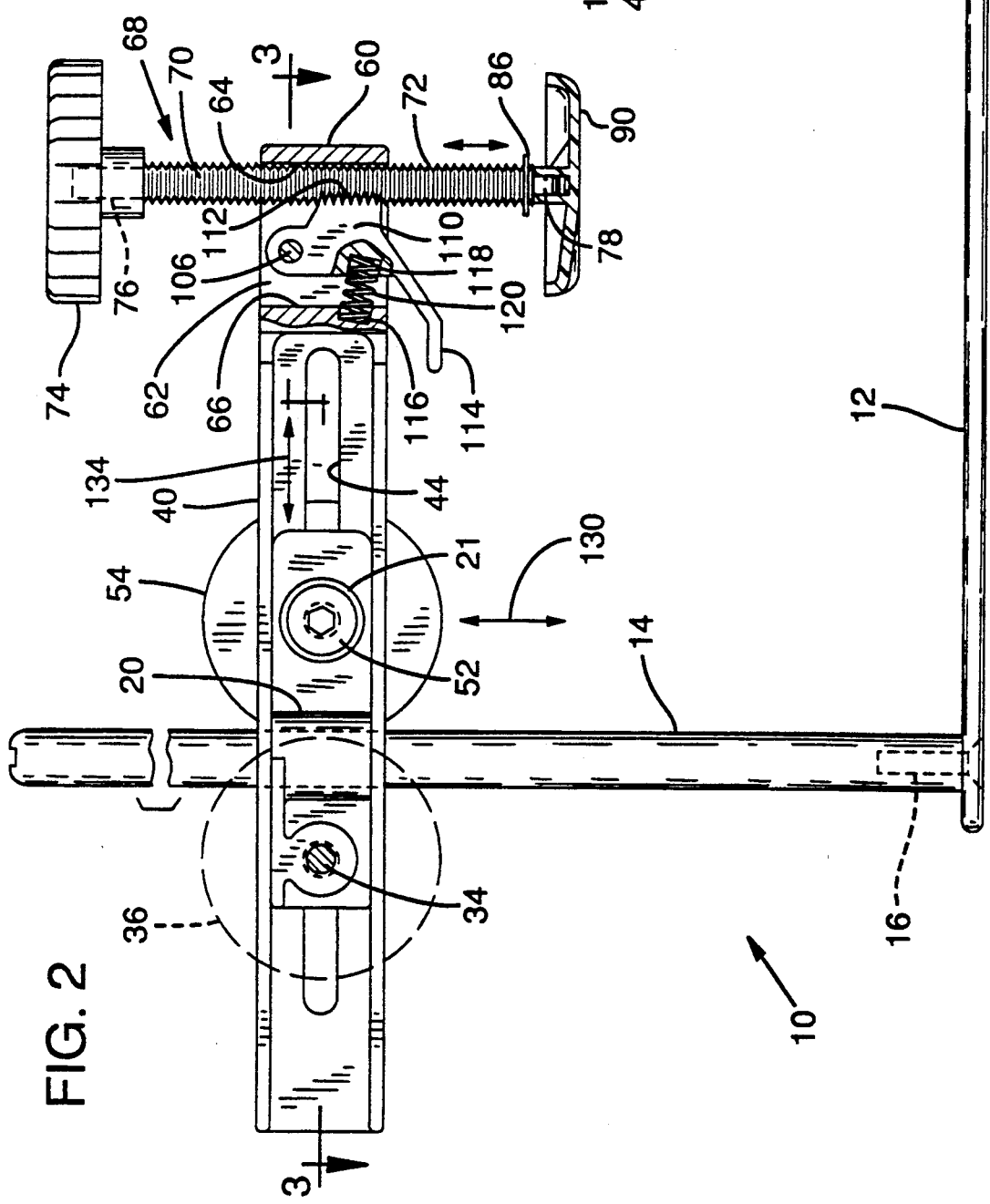
FIG. 2 is a sectional side view of the artery clamp of FIG. 1 showing the carrier and quick release feed mechanism in the engaged position.
Figure 3:
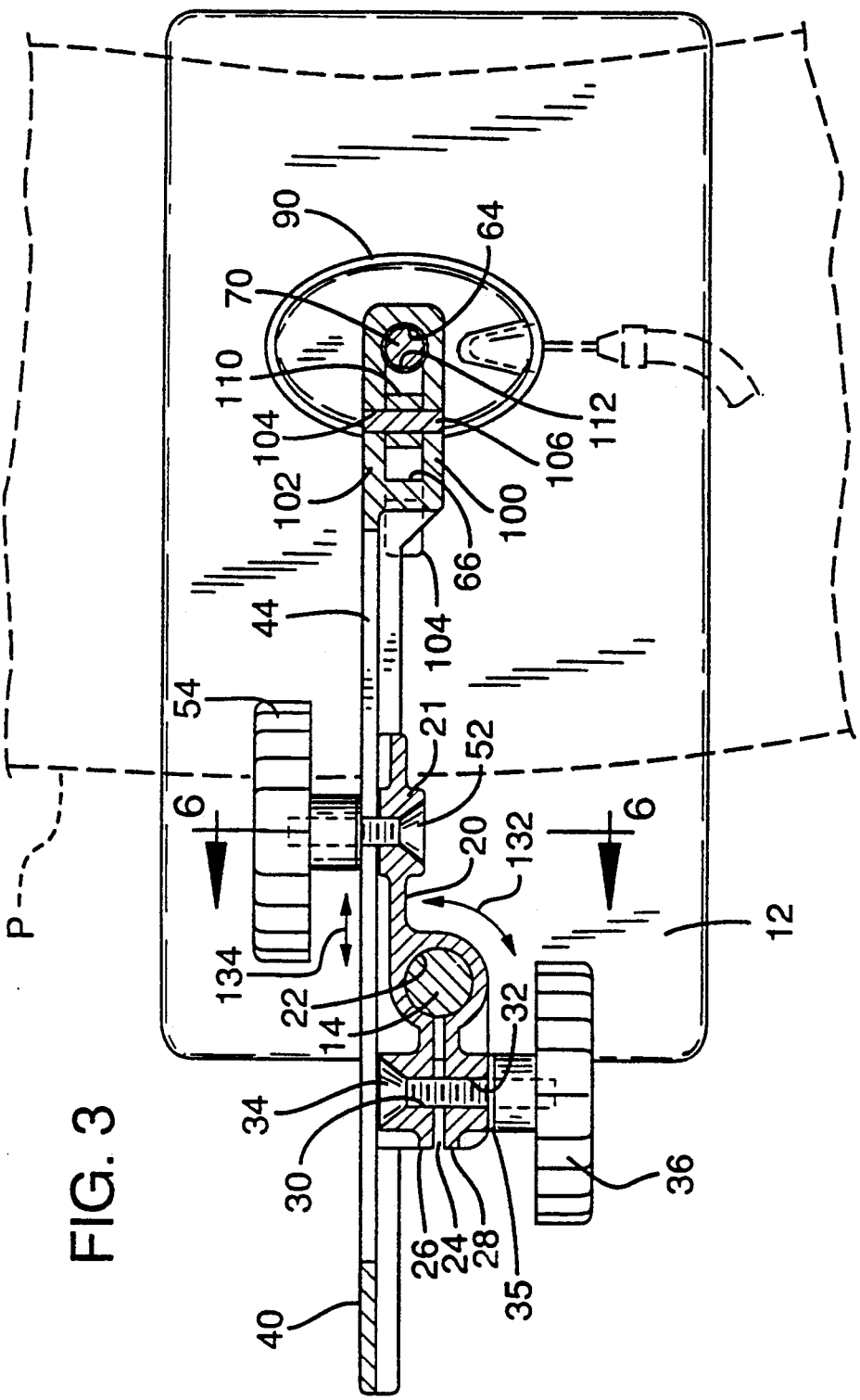
FIG. 3 is a top sectional view of the artery clamp as viewed on view lines 3—3 of FIG. 2.

Referring also to FIGS. 2, 2A and 3, the clamp 10 has a thin flat rectangular base 12. A cylindrical column 14 extends normally from and is fixedly attached near one end of the base 12 by a fastener 16 as illustrated in FIG. 2. A carriage 20 is movably mounted on the column 14, with the carriage 20 being moveable upwardly and downwardly on the column 14 as indicated by the directional arrow 130 and also being pivotally moveable in reference to the column 14 as indicated by the directional arrow 132. The carriage 20 is movably mounted on the column 14 with the column 14 fitting in a bore 22 (best seen in FIG. 3) provided in the carriage 20. As shown in FIG. 3 a slit 24 is provided in one end of the carriage 20 that communicates with the bore 22. The slit 24 provides a separation between end portion 26 and end portion 28 of the carriage 20. A chamfered threaded bore 30 is provided in the end portion 26 of the carriage 20 that is aligned with a bore 32 in the end portion 28 as shown. A lock screw 34 is threadably installed in the bore 30 with an end of the lock screw 34 extending through the bore 32, the bore 32 being larger than the bore 30 permitting the lock screw 34 to be slidably received in the bore 32. A washer 35 and lock knob 36 is threadably installed on the end of the lock screw 34. Clamping of the carriage 20 in a fixed position on the column 14 is achieved by tightening the knob 36 on the screw 34 which forces the end portions 26 and 28 toward each other causing bore 22 to reduce in size to affect clamping of the carriage 20 to the column 14.

The carriage 20 is arranged for the moveable mounting of a radial arm 40. The arm 40 is mounted to the carriage 20 with the arm 40 extending in a parallel attitude with respect to the base 12. The arm 40, as seen in FIGS. 1, 2 and 6, has a channel portion 42 or U shape for mounting and guiding the arm 40 on the carriage 20. An elongate slot 44 having a length substantially as illustrated in FIGS. 1-3 is provided in the channel portion 42. A side 21 of the carriage 20 is sized to fit in the channel portion 42 of the arm 40 as shown in FIG. 6. A chamfered threaded bore 50 is provided in the carriage 20 that extends through side 21 for receiving a threaded lock bolt 52. The lock bolt 52 is threadably installed in the bore 50 and is of sufficient length to extend through the slot 44 in channel portion 42 of the arm 40 when the arm 40 is mounted on the carriage 20. A washer 53 and lock knob 54 is loosely threadably installed on the end of the lock bolt 52 to loosely engage the surface 46 of the channel portion 42 of the arm 40 to retain the arm 40 on the carriage 20. With the lock knob loose, the arm 40 may be adjusted along the carriage 20 as indicated by directional arrow 134 to any position within its travel limits. The ends of the slot 44 engaging the lock bolt 52 define the travel limits. The arm 40 is frictionally clamped to the carriage 20 in an adjusted position by tightening the lock knob 54.

With reference to FIGS. 1, 2, 2A, and 3 an end 60 of the arm 40 is configured for a quick release adjusting mechanism, such as a feed nut 110, and the mounting of a pressure pad carrier 68. As shown the end 60 extends from and is greater in width than the channel portion 42 of the arm 40 and has a formed elongate slot 62. The slot 62 is basically rectangular in section having an enlarged circular end or bore 64. The enlarged circular end 64 has a diameter greater than the width of the slot 62. The end 64 is sized to receive the threaded pressure pad carrier 68 with the carrier 68 being slidable in the end 64. The carrier 68 comprises an elongate rod 70 having threads 72 formed thereon excepting for the ends 76 and 78. The diameter of the threaded portion 72 of the carrier 68 is greater than the width of the slot 62 so that the carrier 68 is captive in the end 64 of the slot 62. A knob 74 is fixedly attached to the end 76 of the rod 70 in a conventional manner such as by adhesive bonding. The opposite end 78 of the rod 70 is reduced in diameter as shown in FIG. 4 and has a spherical end 80. A groove 82 is formed adjacent the spherical end 80. A groove 84 is provided in the threaded portion near end 78 for receiving a snap ring 86.

A pressure pad 90 is removably and rotatably mounted on the spherical end 80 of the carrier 68. The pad 90 has a bore 92 sized to loosely receive the end 78 of the carrier 68 permitting the pad 90 to rotate on the end 78. Projections 94 are provided in the bore 92 that will enter the groove 82 when the pad 90 is installed on the end of the carrier 68. The projections 92 will yieldably retain the pad on the carrier 68. The pad 90 may thus be snapped on and snapped off the end 78 of the carrier 68.

Referring again to FIGS. 2 and 2A, the sides 100 and 102 of the end 60 adjacent the slot 62 of the arm 40 have a through bore 104 for receiving a mounting shaft 106. The shaft 106 bridges the slot 62 (see FIG. 3) and a feed nut 110 is pivotally mounted on the shaft with the feed nut being positioned in the slot 62. As seen in FIGS. 2 and 2A, the nut 110 has a threaded portion 112 engageable and dis-engageable with the threads 72 of the carrier 68. A lever 114 is formed on the feed nut 110 to facilitate pivoting the feed nut 110 on shaft 106. The lever 114 is utilized to pivot the feed nut 110 out of engagement with the threads 72 on carrier 68. As shown, the lever 114 extends below (as viewed in the figures) the end 60 of the arm 40. A recess such as a bore 116 is provided in the end 66 of the slot 62 and a corresponding recess or bore 118 is provided in the feed nut 110. The bores 116 and 118 are provided for receiving a biasing member such as the ends of a compression spring 120. The spring 120 having its ends fitting in the bores 116, 118 will urge the nut 110 to pivot on the shaft 106 and thus will urge nut 110 into engagement with the carrier 68, that is the threads 112 of the nut 110 will be engaged with the threads 72 of the carrier rod 70. The pad 90 mounted on the carrier 68 may be finely adjusted in relation to the arm 40 (or to a puncture site in an artery) when the nut 110 is in engagement with the carrier 68. The fine adjustment to either advance the pad 90 toward the puncture site or to retract the pad 90 from the puncture site is accomplished by rotation of the knob 74. The pad 90 mounted on the carrier 68 may be rapidly advanced toward or rapidly retracted from a puncture site by dis-engaging the feed nut 110 from the carrier 68 and simply sliding the carrier 68 in the bore 64 in the desired direction. The pivotal mounting arrangement of the feed nut 110 on the arm 40 also permits the rapid downward advance of the carrier 68 by urging the carrier downward (as viewed in the figures) such as by pushing down on the knob 74. The force applied will cause the nut 110 to yieldably pivot out of positive engagement with carrier one thread form at a time. The feed nut 110 will be pivoting in a ratcheting manner into and out of engagement with the carrier as the carrier is forced downward. This arrangement is provided by the feed nut 110 being pivoted at a point above the threaded portion 112 whereby the spring 120 urges the nut 110 to pivot upwardly against the carrier 68. Thus an upwardly directed force on the carrier 68 will, in contra distinction, further tighten the nut on the carrier and prevent release.

The clamp 10 is easily and rapidly adjusted. The independent locking or clamping of the carriage 20 to the column 14 and the independent locking or clamping of the arm 40 to the carriage 20 provides for adjustments to either without disturbing the adjustment made to the other. The releasable nut 110 provides for both rapid movement and finely controlled movement of the carrier 68. With the nut dis-engaged the carrier 68 may be rapidly moved in the bore 64 which provides for rapid advancement or retraction of the pressure pad 90 toward and away from the puncture site such as made in a femoral artery. With the nut 110 engaged with the carrier 68, the movement of the carrier 68 may be finely adjusted by rotating the carrier knob 74. The fine adjustment of the movement of the carrier 68 is utilized to control the pressure applied to the puncture by the pad 90.

A typical setup and operational procedure for the clamp 10 includes elevating the carrier 68 to its upper position by pivotally disengaging the nut 110 from the carrier 68 and sliding the carrier 68 upward by grasping the knob 74. The snap ring 86 installed in the groove 84 of the rod 70 limits the upward movement of the carrier 68 by engaging the underside of the end 60 of the arm 40. The carriage 20 with the mounted arm 40 are elevated by loosening the locking knob 36 which unclamps the carriage from the column 14. The assembly of the carriage 20 and arm 40 may thus be elevated and/or pivoted on the column 14 to a desired position. The lock knob 36 is tightened to hold the carriage and arm assembly in the adjusted position. The base 12 of the clamp 10 is slid under the patient strategic to the puncture site, generally as illustrated in FIG. 3, the patient being designated by the dashed outline labeled P. The base 12 of the clamp 10 is supported on the item supporting the patient such as a table. The portion of the patient resting on the base 12 will hold the base of the clamp 10 in position. The locking knob 36 is loosened to allow the positioning of the carriage 20 (with the arm 40) on the column, making vertical and pivotal adjustments as required. The locking knob 36 is tightened to secure the carriage 20 in the adjusted position on the column 14. The position of the arm 40 may now be adjusted laterally by loosening the locking knob 54. This allows the arm 40 to be adjusted on the carriage to its desired position. The pressure pad 90 may be rapidly advanced toward the puncture site by pivoting the nut 110 out of engagement with the carrier 68. This allows the carrier 68 to be rapidly slid in the bore to advance the pressure pad 90 rapidly toward the puncture site. In the alternative, the carrier 68 may be rapidly advanced downward by applying a force to the knob 74 which will cause the feed nut 110 to yieldably dis-engage. When the pad 90 is near the puncture site or the pad 90 is in contact with the skin of the patient surrounding the puncture site, the nut 110 is allowed to pivot into engagement with the carrier 68. The pressure pad 90 may now be finely adjusted to apply the desired pressure by rotation of the carrier 68 by using knob 74.

Those skilled in the art will recognize that variations and modifications may be made without departing from the true spirit and scope of the invention. The invention is therefore not to be limited to the embodiments described and illustrated but is to be determined from the appended claims.

What is claimed is:

1. An artery clamp for applying pressure to an artery of a member of a patient, comprising;
    a base;
    a column extending upwardly and fixedly attached to the base;
    an arm extending from said column adapted to overlie the member of the patient resting on said base;
    a carrier including a rod, said arm provided with a configured guide opening mated to said rod and permitting vertical sliding axial movement only of said rod whereby the carrier is adjustably mounted to the arm overlying said member and adjustably movable toward and away from said member;
    a pressure pad on a lower end of said rod to be moved by said rod into engagement with said member;
    an adjusting mechanism mounted to said arm and in engagement with said rod for controlling adjustment of said carrier relative to said arm;
    said adjusting mechanism having mutually exclusive dual adjusting functions including a first adjusting function for controlled adjustment of the pressure pad toward and away from the member and a second adjustment function manually engageable to release and first adjustment and provide rapid adjustment of the pressure pad.

2. An artery clamp as defined in claim 1, wherein;
    the rod has a threaded shaft and the first adjustment function is provided by a female threaded nut having a threaded portion, said nut movably mounted on said arm and a biasing member urging said threaded portion of said nut into threadable engagement with said threaded shaft.

3. An artery clamp as defined in claim 2, wherein;
    the nut is pivotally mounted for pivoting the nut around a pivot point positioned above said threaded portion which is pivoted upwardly and inwardly toward said shaft to achieve engagement with said shaft and is pivoted downwardly and outwardly away from said shaft to achieve disengagement with said shaft thereby permitting a downward force on the carrier to effect release of the nut and whereby an upward force tightens the engagement of the nut with the shaft.

4. An artery clamp as defined in claim 3, wherein;

said biasing is provided by a spring member urging pivoting movement of said nut toward said shaft; and, a lever extends from said nut, said lever manually engageable to force pivoting of said nut away from said shaft and out of engagement with said shaft.

5. An artery clamp as defined in claim 4, further including;

a carriage movably mounted on the column;

said arm movably mounted on the carriage.

6. An artery clamp as defined in claim 5, further including;

a carriage clamping mechanism;

an arm clamping mechanism; and, said carriage clamping mechanism and said arm clamping mechanism separately operable.

7. An artery clamp as defined in claim 3 wherein the configured guide opening is provided by a slot that extends vertically through the arm, said slot having an enlarged end that is cylindrically shaped with a diameter greater than the remainder of the slot width and mated to the diameter of the shaft whereby the shaft is confined for axial movement only through the configured end of the slot, said nut mounted in the slot of the arm and said threaded portion adapted for pivotal movement into said end of the slot and into engagement with the threaded shaft of said rod.

* * * * *